United States Patent [19]
Schwartz et al.

[11] Patent Number: 5,753,520
[45] Date of Patent: May 19, 1998

[54] PROTEIN LABELLING

[75] Inventors: David A. Schwartz, Exton; Michael J. Abrams, Glenmore; Christen M. Giandomenico, Exton, all of Pa.; Jon A. Zubieta, Albany, N.Y.

[73] Assignee: Johnson Matthey Inc., Valley Forge, Pa.

[21] Appl. No.: 384,641

[22] Filed: Feb. 6, 1995

Related U.S. Application Data

[62] Division of Ser. No. 26,426, Mar. 4, 1993, Pat. No. 5,420, 285, which is a continuation of Ser. No. 888,282, May 26, 1992, Pat. No. 5,206,370, which is a continuation of Ser. No. 483,201, Feb. 21, 1990, abandoned, which is a continuation-in-part of Ser. No. 315,270, Feb. 24, 1989, abandoned.

[51] Int. Cl.[6] .................... C07K 16/00; C07K 17/00
[52] U.S. Cl. .................... 436/542; 436/804; 530/387.1; 530/391.1; 530/391.5; 530/395; 534/14
[58] Field of Search .................... 530/387.1, 395, 530/391.1, 391.5; 436/542, 804

[56] References Cited

U.S. PATENT DOCUMENTS

| | | | |
|---|---|---|---|
| 4,749,647 | 6/1988 | Thomas et al. | 435/6 |
| 4,861,869 | 8/1989 | Nicolotti et al. | 424/1.53 |
| 5,514,676 | 5/1996 | Ulrich et al. | 514/231.2 |

FOREIGN PATENT DOCUMENTS

| | | | |
|---|---|---|---|
| 8226387 | 6/1988 | Australia | 436/534 |
| 9188256 | 7/1986 | European Pat. Off. | 436/545 |
| 0271806 | 6/1988 | European Pat. Off. | |
| 2101118 | 1/1983 | United Kingdom | 546/324 |

OTHER PUBLICATIONS

King et al. Biochemistry. 25:5774–5779 (1986).
Arano et al., J. of Nuclear Medicine, 28(6):1027–1033 (Jun. 1987).
Arano et al. Appl. Radiat. Isot., 37(7):587–592 (1986).
Eckelman et al. Nucl. Med. Biol. 16(2):171–176 (1989).
Lanteigne et al., Int. J. Appl. Radiat. Isot., 35(7):617–621 (1984).
Chemical Abstracts, vol. 67 (No. 7) Abst. No. 31, 163t, Aug. 14, 1967.
Chemical Abstracts, Vo. 85 (No. 9) Abst. No. 85:63001(b) Aug. 30, 1976.
Chemical Abstracts, vol. 101 (No. 11) Abst. No. 101–90524e, Sep. 10, 1984.
Babich et al. The Journal of Nuclear Medicine, vol. 34, No. 11, pp.–1964–1974, Nov. 1993.

*Primary Examiner*—Alan L. Rotman
*Attorney, Agent, or Firm*—Cushman Darby & Cushman IP Group Pillsbury Madison & Sutro LLP

[57] ABSTRACT

Bifunctional aromatic compounds which are capable of linking metal ions to biologically useful molecules. The bifunctional compounds are characterized as having a hydrazine or hydrazide group and a protein reactive group. The hydrazine or hydrazide group may be protected as a lower alkyl hydrazone. Conjugates of the bifunctional compounds with macromolecules are also described and labelled macromolecules comprised of the conjugates and metal ions are provided. Additionally, a method is provided for forming a labelled macromolecule by reacting a conjugate with a metal species. The compounds and method of this invention are particularly useful in the fields of biology and medicine for imaging and/or therapy.

18 Claims, 7 Drawing Sheets

PROTEIN LABELLING

This is a division of application Ser. No. 08/026,426, filed Mar. 4, 1993, now U.S. Pat. No. 5,420,285 which is a continuation of application Ser. No. 07/888,282, filed May 26, 1992, now U.S. Pat. No. 5,206,370, which is a continuation of Ser. No. 07/483,201, filed Feb. 21, 1990, now abandoned, which is a continuation-in-part of Ser. No. 07/315,270, filed Feb. 24, 1989, now abandoned.

BACKGROUND OF THE INVENTION

This invention relates to bifunctional compounds capable of linking metal ions, particularly technetium and rhenium, to biologically useful molecules.

Because of their high biological specificity, certain macromolecules (e.g., monoclonal antibodies) have been used to target radioisotopes to specific in vivo sites for the purpose of imaging and/or therapy. The use of the metastable isotope of technetium, $^{99m}$Tc, in diagnostic nuclear medicine is well established and the beta-emitting isotopes of rhenium $^{186}$Re, $^{188}$Re and $^{189}$Re can be used therapeutically. A number of methods for attaching technetium to macromolecules have been described. Some of these methods involve the reduction of disulfide groups in the macromolecule (usually an immunoglobulin) to thiols and the subsequent use of these groups to bind reduced Tc (e.g., McKenzie et al., International Publication #WO 87/04164; and Bremer et al., EPO 271 806 A2). Methods of this type have several potential disadvantages. The reduction of disulfide units can lead to protein de-naturation and a subsequent loss in biological specificity. Also, the method cannot be used to label macromolecules lacking disulfide moieties.

Alternatively, $^{99m}$Tc can be linked to macromolecules via bifunctional chelates such as DTPA (D. Lanteigne and D. J. Hnatowich, Int. J. Appl. Radiat. Isot., Vol. 35(7), p. 617 (1984), chelating thiosemicarbazones (Y. Arano et al., Int. J. Nucl. Med. Biol., Vol. 12, p. 425 (1985), and diamide-dithiol ligands (A. Fritzberg, European Patent Appl. EP 188256 2A). Problems associated with these methods include significant nonspecific binding of technetium (binding to the protein at sites other than the chelating group) and slow kinetics of Tc-labelling.

Accordingly, it is the object of the present invention to provide new bifunctional molecules having hydrazine or hydrazide groups and protein reactive groups which can be used to link metal ions, such as $^{99m}$Tc, to macromolecules.

Another object of the present invention is to provide a method for labelling macromolecules with metal ions in which binding of the metal at sites other than the chelating group is minimal, and in which labelling occurs at a relatively fast rate (less than one hour at room temperature).

SUMMARY OF THE INVENTION

According to the invention, novel bifunctional hydrazine and hydrazide compounds, as well as conjugates thereof, are provided. Methods of labelling the conjugates with metal ions are also provided.

Broadly, the hydrazine and hydrazide compounds described herein are bifunctional aromatic hydrazines or hydrazides having a protein reactive substituent and a negative counterion. A modification of this invention is also provided in which the hydrazine or hydrazide function is protected as a lower alkyl hydrazone.

In another embodiment of the invention, conjugates are formed by reacting bifunctional hydrazine or hydrazide compounds of the invention with macromolecules such as proteins, polypeptides or glycoproteins. The bifunctional compounds react with nucleophilic groups on the macromolecules (e.g. lysine residues) to yield conjugates containing free hydrazine/hydrazide groups.

In a third embodiment, labelled macromolecules comprised of conjugates and metal ions are formed.

In a fourth embodiment, a method is provided for labelling macromolecules by reacting a conjugate of the invention with a metal species.

DETAILED DESCRIPTION OF THE INVENTION

The novel hydrazine and hydrazide compounds of the present invention are represented by one of the following formulas (I) or (II):

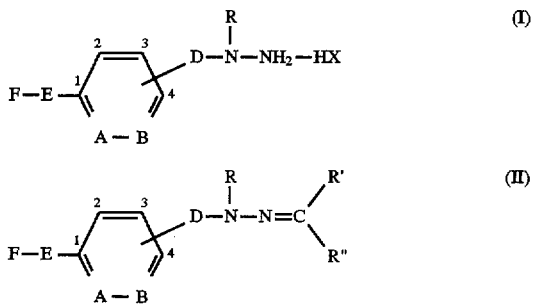

wherein:

A is a carbon or nitrogen atom;

B is a carbon or nitrogen atom;

D is a direct bond (to the 2-, 3-, or 4-position of the ring), $CH_2$, C=O or

E is C=O or together with F forms a maleimidyl group;

F is a group readily replaced by a primary amine in neutral or basic aqueous media when E is C=O or together with E forms a maleimidyl group;

R is hydrogen or a lower alkyl group;

R' and R" may be the same or different and are selected from hydrogen and lower alkyl; and X is a negative counterion.

Another embodiment of the invention includes compounds of the formula (III):

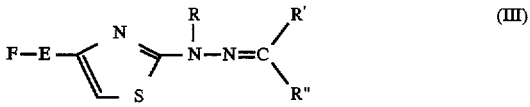

where R, R', R", E and F have the values given above.

When E is carbonyl C=O, F is any group which, in combination with the attached carbonyl group, forms an active ester or active amide. Examples of suitable species for F include such diverse groups as N-oxysuccinimidyl, tetrafluorophenolate, N-oxybenztriazole and imidazolate. These examples are not intended to be construed as limiting the scope of the invention.

Suitable groups for R, R' and R" include, but are not limited to, the following: H, $CH_3$, $C_2H_5$, and $C_3H_7$.

Examples of useful X ions are halides, nitrate, trifluoroacetate, tetrafluoroborate and sulfate. These examples are not intended to limit the scope of suitable counterions.

The above-described compounds are stable, isolable derivatives of molecules that contain two cross-reactive moieties: a hydrazine/hydrazide group and a protein reactive group such as an active ester, active amide or maleimido group.

In the synthesis of these stable derivatives, an acid labile protecting group such as t-butoxycarbonyl (t-BOC) is removed from the hydrazine/hydrazide under anhydrous acidic conditions, leaving the protein reactive group unchanged and the hydrazine/hydrazide group in an unreactive, protonated form. Alternatively, the hydrazine/hydrazide group can be protected as a lower alkyl hydrazone.

When a bifunctional compound having a protonated (or hydrazone protected) hydrazine/hydrazido function is then combined with a macromolecule such as a protein, polypeptide or glycoprotein in neutral or slightly basic media, preferably a pH of about 7–8.5, the protein-reactive part of the compound will react with nucleophilic groups on the protein, polypeptide or glycoprotein (e.g., amine groups such as lysine residues) to yield a conjugate containing free hydrazine/hydrazide groups. In the case of hydrazone conjugates, the free hydrazine/hydrazide is formed by dialysis into an acidic (pH 5.6) buffer. Because this type of conjugate includes a hydrazine or hydrazide, a strong metal binding group, it will then readily react when mixed with a suitable metal species in acidic media to yield a labelled protein, polypeptide or glycoprotein.

The metal species may be, for example, a reduced Tc species formed by reacting $TcO_4^-$ with a reducing agent, for example, stannous ion, in the presence of a chelating oxygen ligand (e.g. glucoheptonate). Examples of suitable reduced Tc species include Tc-glucoheptonate, Tc-gluconate, Tc-2-hydroxyisobutyrate, Tc-lactate and Tc-4,5-dihydroxy 1,3-benzene disulfonate. Other metals and ligands are also within the scope of the invention.

A Tc labelling process can be conveniently performed in an aqueous buffer, preferably at a pH of about 4.5–6.5, in one hour or less. Reaction with other suitable metal species occurs in a similar manner under similar conditions.

Radiochemical yield as determined by high performance liquid chromatography (HPLC) and thin layer chromatography (TLC) using Tc is $\geq 90\%$. Treatment of protein with nonlinkable analogs, (i.e., compounds without a protein reactive carbonyl group, such as 4-hydrazinobenzoic acid or 6-hydrazinopyridine-3-carboxylic acid) does not yield protein capable of significant Tc binding, thus demonstrating the high specificity of this technique.

The technetium atoms are believed to be bound to the conjugate via a hydrazido or diazenido linkages:

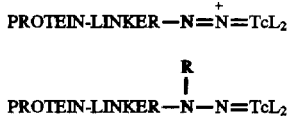

Wherein:

L is an ancillary dioxygen ligand.

Examples of this type of linkage have been described for Mo and Re (*Comprehensive Coordination Chemistry*, Vol. 2, G. Wilkinson, ed., Pergamon (Oxford) 1987, p. 130–151) and several analogous complexes of $^{99}Tc$ have been prepared by the reaction of an organohydrazine derivative and a Tc(V) oxo species.

The above labelling scheme has been used to label polyclonal human IgG and the Fc region of human IgG. The Tc-conjugates have been used to image focal sites of infection in a rat model. The labelling scheme has also been used to label fragment E, (see L. C. Knight et al, *J. Clin. Invest.*, Vol. 72, 1983, p. 2007–2013) which was used to image thrombi in a rabbit model for deep vein thrombosis and the monoclonal antibody 5E8.

EXAMPLES

The NMR and IR data given in the examples was obtained as follows:

$^1H$ NMR spectra were recorded on an 80 MHz IBM AF-80 Spectrometer. All $^1H$ NMR results were recorded in DMSO-$d_6$ unless otherwise indicated. IR spectra were recorded on a Perkin-Elmer 598 infrared spectrometer. NMR and IR spectra were consistent with assigned structure.

Compound names given in brackets below the title compounds in the various examples conform to Chemical Abstracts service index nomenclature. Reaction schemes are illustrated in the accompanying drawings wherein each FIGURE shows the preparation of an individual compound according to the invention. Thus:

Example 1

Preparation of succinimidyl 4-hydrazinobenzoate hydrochloride hydrochloride

[2,5-pyrrolidinedione, 1-[(4-hydrazinobenzoyl)oxy]-monohydrochloride]

Figure 1:
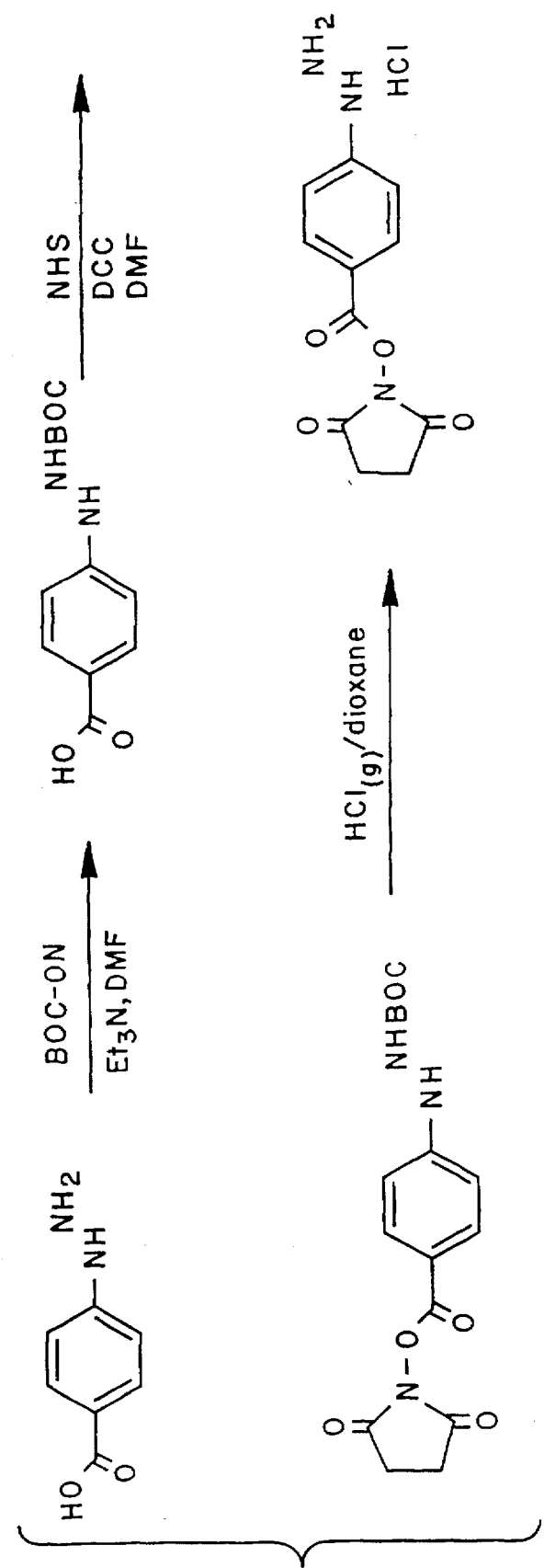
FIG. 1 illustrates the reaction for the preparation of succinimidyl 4-hydrazinobenzoate hydrochloride.
Figure 2:
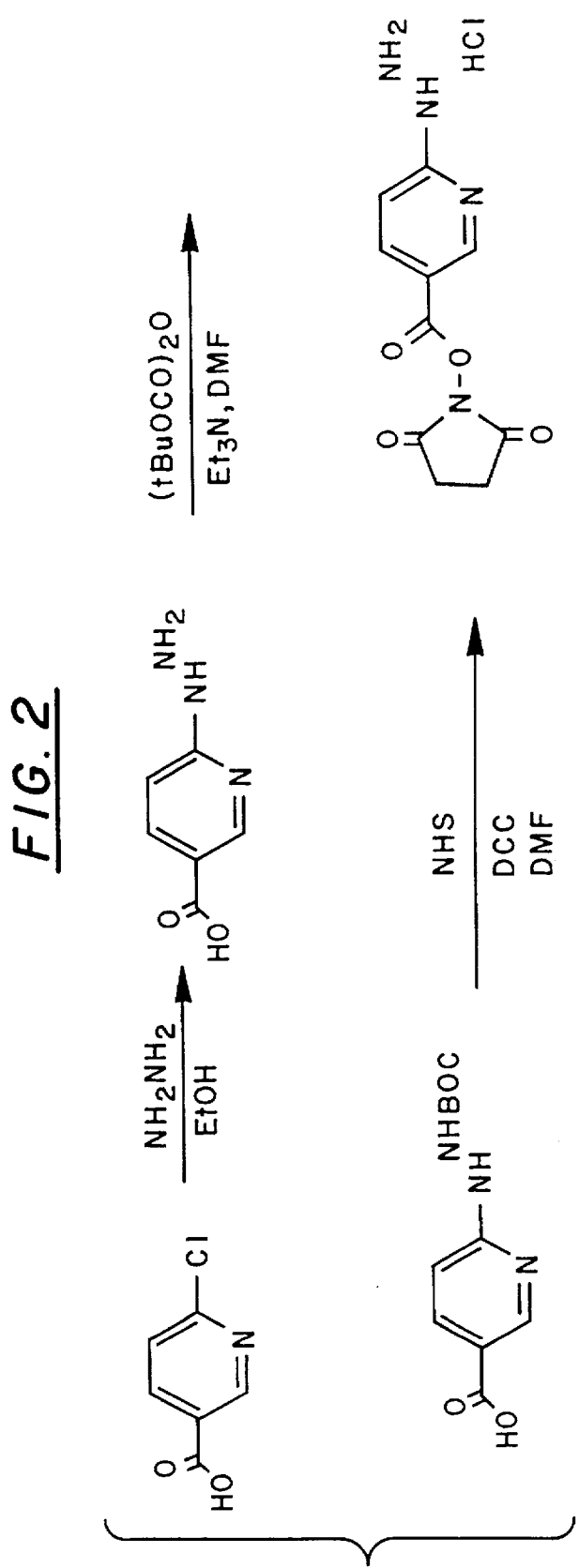
FIG. 2 illustrates the reaction for the preparation of succinimidyl 6-hydrazinopyridine-3-carboxylate hydrochloride.
Figure 3:
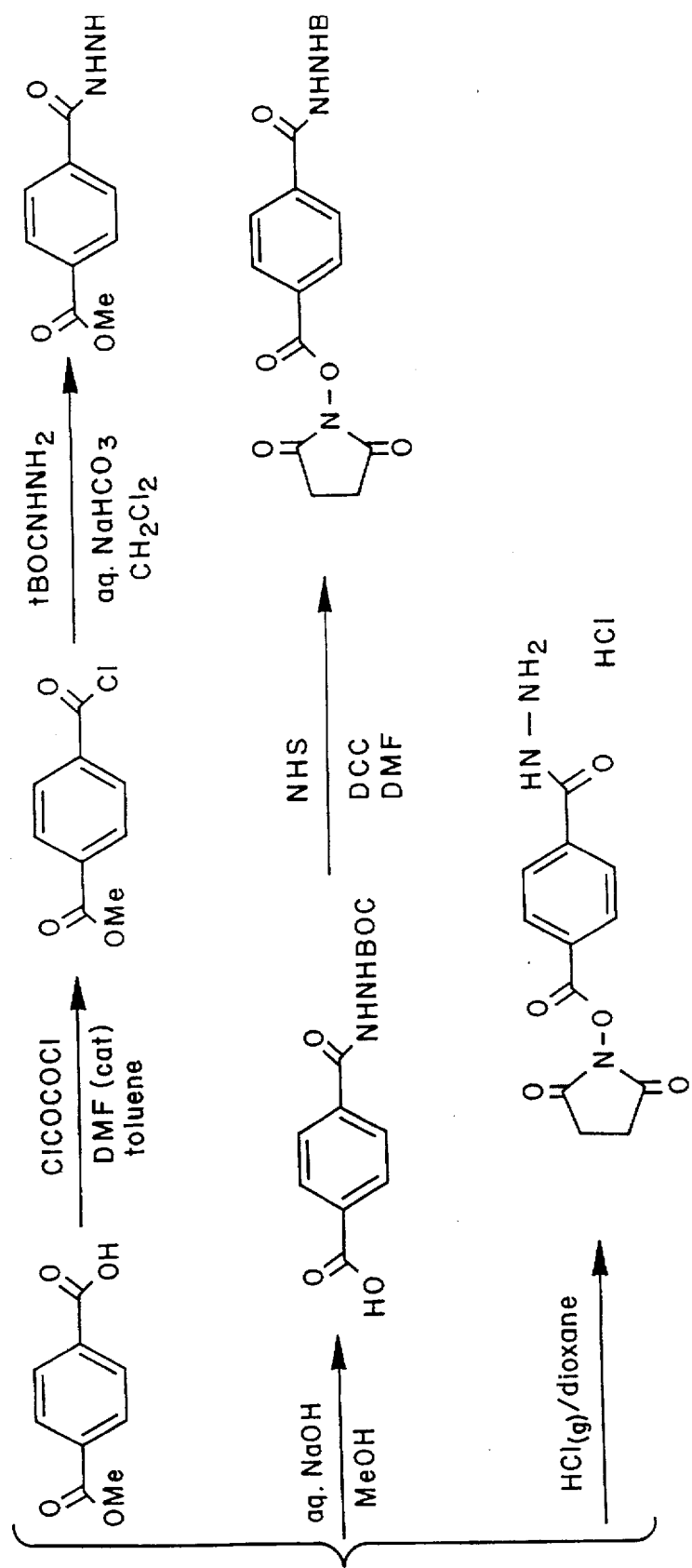
FIG. 3 illustrates the reaction for the preparation of succinimidyl 4-hydrazidoterephthalate hydrochloride.
Figure 4:
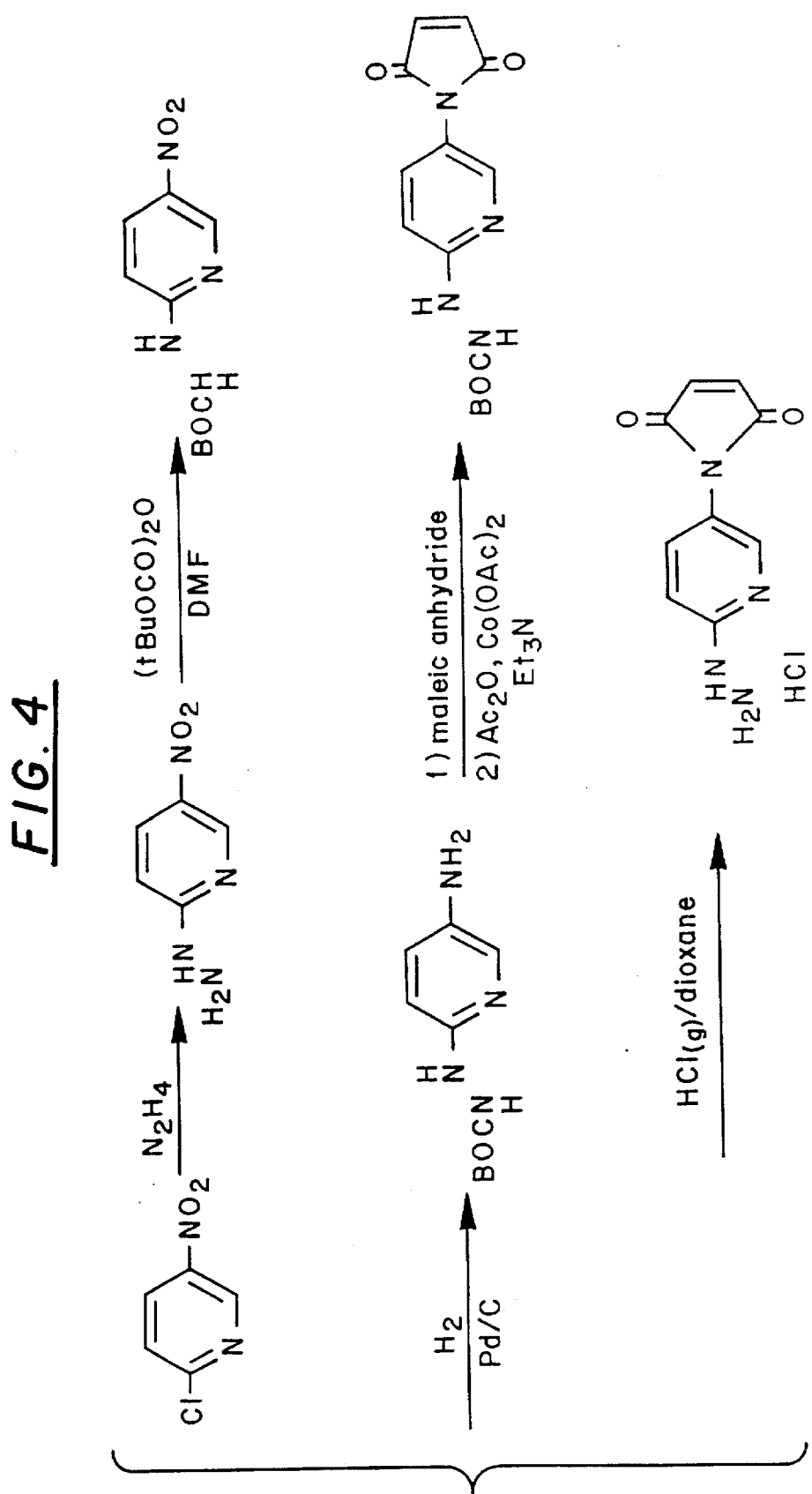
FIG. 4 illustrates the reaction for the preparation of 5-maleimidyl-2-hydrazinopyridine hydrochloride.
Figure 5:
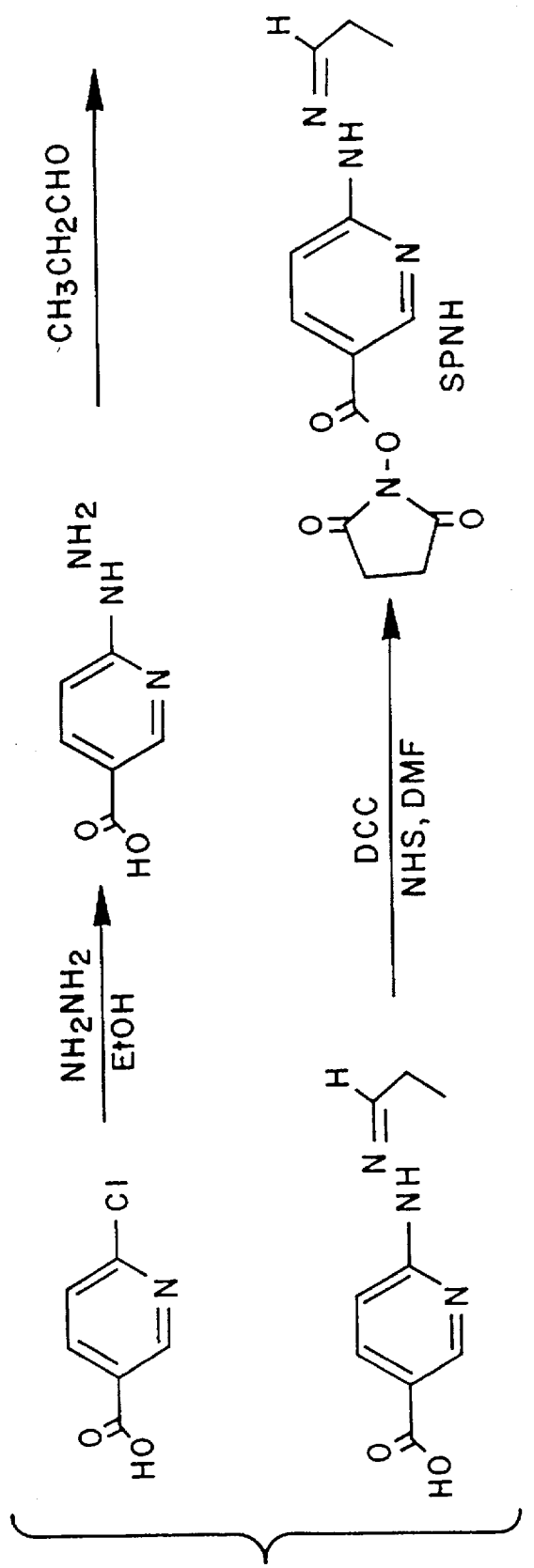
FIG. 5 illustrates the reaction for the preparation of succinimidyl 2-(2-propenylhydrazone)nicotinate.
Figure 6:
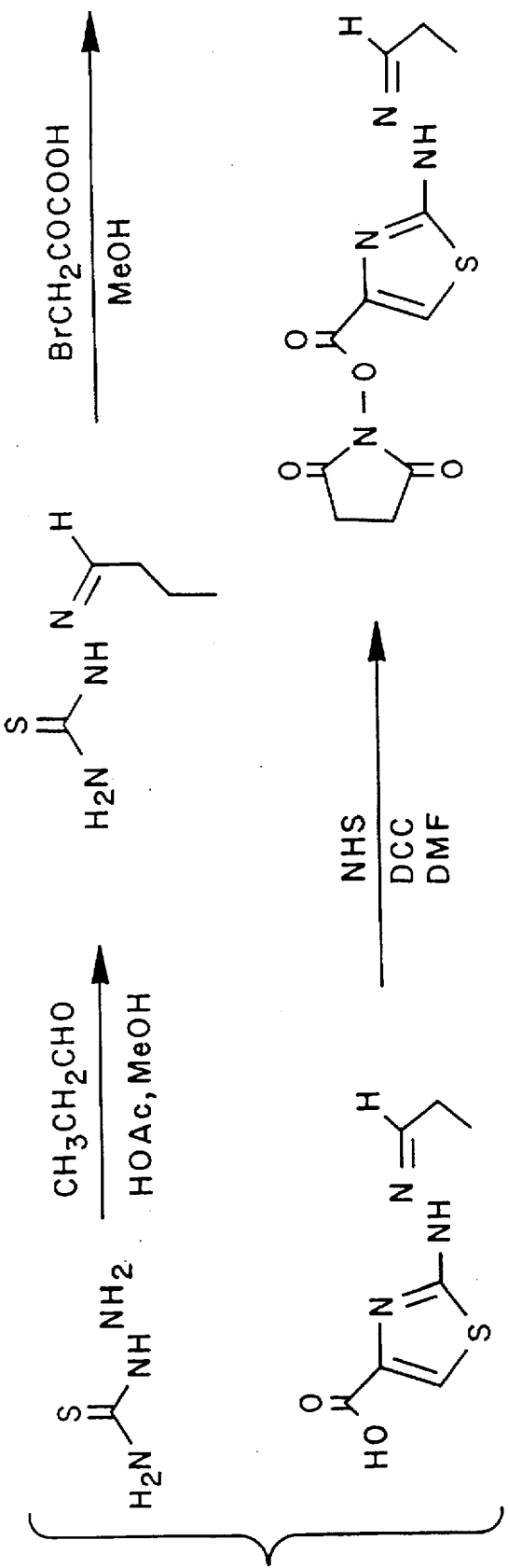
FIG. 6 illustrates the reaction for the preparation of succinimidyl 2-(2-(1-propenyl)hydrazone)-thiazole-4-carboxylate.
Figure 7:
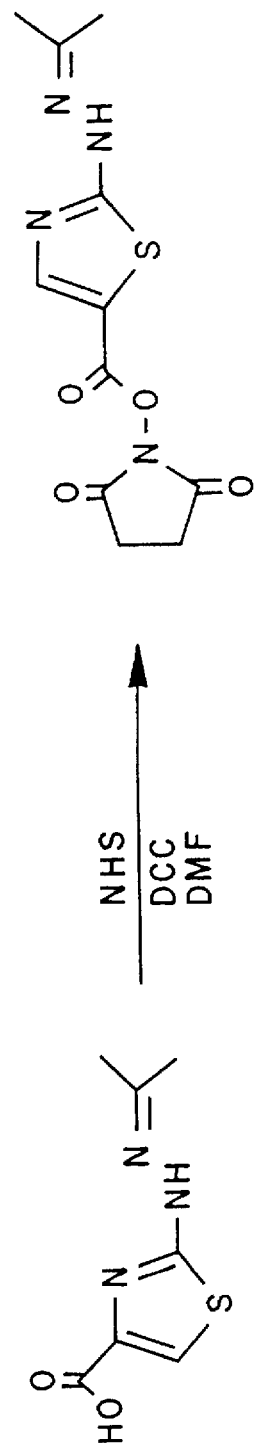
FIG. 7 illustrates the reaction for the preparation of succinimidyl 2-(2-methylethenylhydrazone) thiazole-4-carboxylate.
Figure 8:
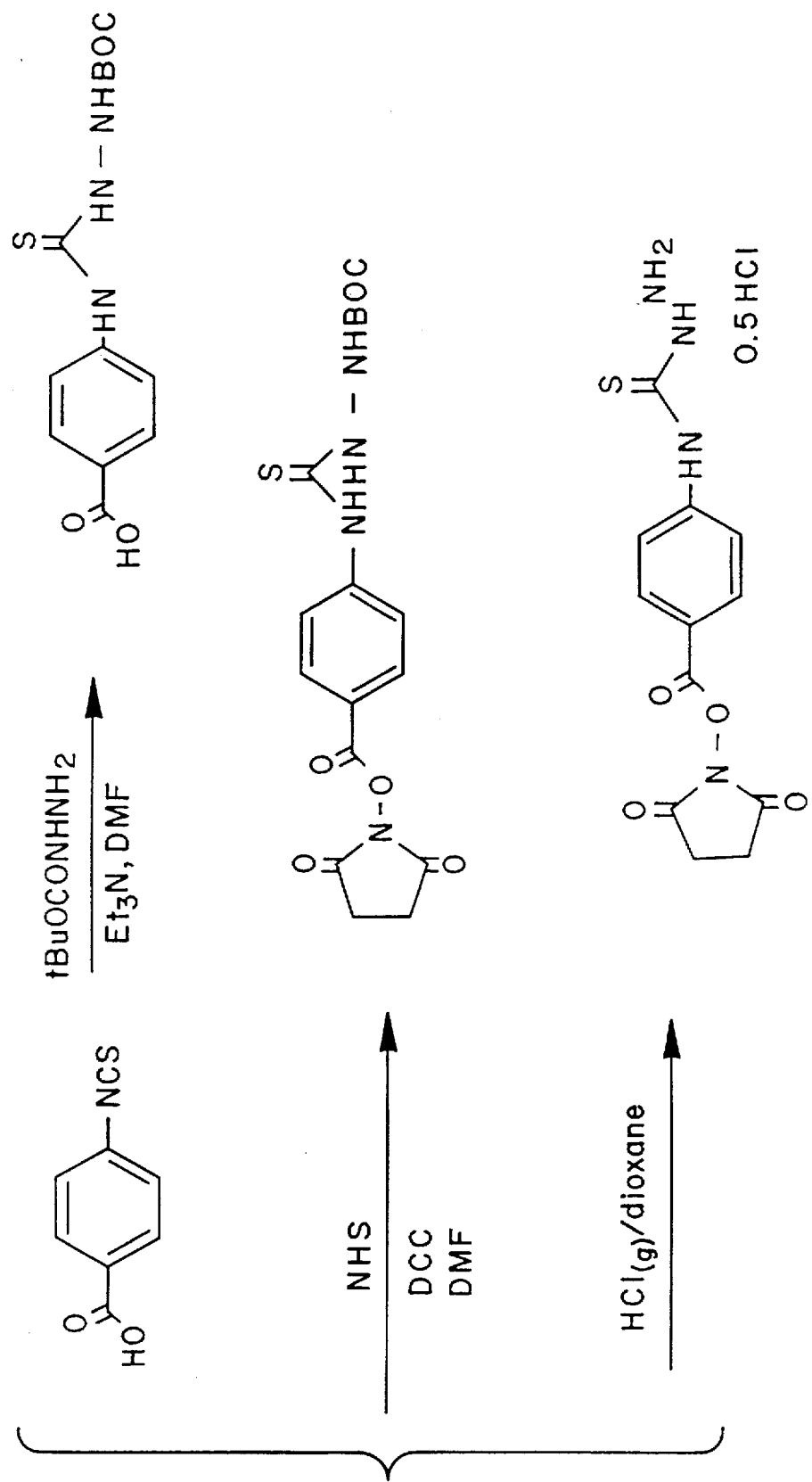
FIG. 8 illustrates the reaction for the preparation of succinimidyl 4-thiosemicarbazidobenzoate hemihydrochloride.

4-Hydrazinobenzoic acid, 2-(t-butoxycarbonyloxyimino)-2-phenylacetonitrile (BOC-ON), dicyclohexylcarbodiimide and N-hydroxysuccinimide were purchased from Aldrich Chemicals (Milwaukee, Wis.).

Synthesis of 4-BOC-hydrazinobenzoic acid

To a stirred solution of 4-hydrazinobenzoic acid (1 equivalent) and triethylamine (3 equivalents) in dimethylformamide (5 mg/l) was added dropwise a solution of BOC-ON (1 equivalent) in dimethylformamide. The reaction mixture was stirred at room temperature for 3 hours. Ten percent aqueous hydrochloric acid was added and subsequently the solution became cloudy. The solution was extracted with ethyl acetate and the combined organic extracts were washed with water, dried over magnesium sulfate, filtered and concentrated under reduced pressure to give a brown solid. The solid was recrystallized from chloroform to give the desired product as a pale brown solid; yield 69%. Analysis: Calculated for $C_{12}H_{16}N_2O_4$:

C - 57.13; H - 6.39; N - 11.10. Found: C - 57.02; H - 6.13; N - 11.61.

$^1$H NMR δ: 1.45(s,9H),6.77(d,$J_{ab}$=8.6 Hz,2H), 7.85(d, $J_{ab}$=8.6 Hz,2H)

Synthesis of succinimidyl 4-BOC-hydrazinobenzoate

[Hydrazinecarboxylic acid, 2-[4-[[(2,5-dioxo-1-pyrrolidinyl)oxy]carbonyl]phenyl]-1,1-dimethylethyl ester]

To a solution of 4-BOC-hydrazinobenzoic acid (1 equivalent) and N-hydroxysuccinimide (1 equivalent) in dioxane (10 ml/g of acid) was added dropwise a solution of dicyclohexylcarbodiimide (1 equivalent) in dioxane (5 ml/g). The reaction mixture was stirred at room temperature for 16 hours. Acetic acid (0.5 ml) was then added and stirring was continued for 1 hour. The reaction mixture was filtered to remove the urea byproduct. The filtrate was concentrated under reduced pressure to give a brown solid which was treated with ether and the solids were isolated by filtration to give a pale brown solid; yield 86%.

Analysis: Calculated for $C_{16}H_{19}N_3O_6$: C - 55.01; H - 5.48; N - 12.03. Found: C - 55.17; H - 5.84; N - 11.86.

$^1$H NMR δ: 1.47(s,9H),2.88(s,4H),6.85(d,$J_{ab}$=8.9 Hz,2H) 8.04(d,$J_{ab}$=8.9 Hz,2H)

Synthesis of succinimidyl 4-hydrazinobenzoate hydrochloride

To a solution of hydrogen chloride in dioxane (50 ml/g of ester; prepared by bubbling hydrogen chloride into dioxane for approximately five minutes) was added succinimidyl 4-BOC-hydrazinobenzoate (1 equivalent). The reaction mixture was stirred at room temperature. The reaction mixture was never homogeneous, however the color was initially pale brown and over 2 hours became orange. The reaction mixture was filtered and washed with ether to give a pale yellow solid; yield 72%; m.p. 203.5°–205° C.

Analysis: Calculated for $C_{11}H_{12}ClN_3O_4$: C - 46.25; H - 4.23; Cl - 12.40; N - 14.71; Found: C - 46.74; H - 4.38; Cl - 12.24; N - 14.26.

$^1$H NMR δ: 2.87(s,4H), 7.05(d,2H,$J_{ab}$=8.9 Hz)7.97(d,2H, $J_{ab}$=8.9 Hz)

Example 2

Preparation of succinimidyl 6-hydrazinopyridine-3-carboxylate hydrochloride

[2,5-pyrrolidinedione, 1-[[(6-hydrazino-3-pyridinyl)carbonyl]oxy]-, monohydrochloride]

6-chloronicotinic acid, di-t-butyl dicarbonate and 85% hydrazine hydrate were purchased from Aldrich Chemicals (Milwaukee, Wis.).

Synthesis of 6-hydrazinopyridine-3-carboxylic acid

6-Chloronicotinic acid (8.0 g) was added to 85% hydrazine hydrate (35 ml). The reaction mixture was placed in a 100° C oil bath for 4 hours. The homogeneous reaction mixture was concentrated to dryness to give a white solid. The solid was dissolved in water and on acidification to pH 5.5 with concentrated hydrochloric acid a precipitate formed. The precipitate was isolated by filtration and the solid was washed with 95% ethanol and ether to give 6.0 g of a pale brown solid; yield 77% m.p. 292°–293° C.;

Analysis: Calculated for $C_6H_7N_3O_2$; C - 47.06; H - 4.61; N - 27.44; Found: C - 46.83; H - 4.38; N - 27.27.

$^1$H NMR δ: 6.69(d,J=8.8 Hz,1H),7.84(dd,J=2.4,8.8 Hz,1H), 8.51(d,J=2.4 Hz,1H)

Synthesis of 6-BOC-hydrazinopyridine-3-carboxylic acid

To a solution of 6-hydrazinopyridine-3-carboxylic acid (1.4 g; 9.8 mmol); triethylamine (1.2 ml; 11.8 mmol) in dimethylformamide (10 ml) was added di-t-butyldicarbonate (2.13 g; 9.8 mmol). The reaction mixture became homogeneous over 1 hour and stirring was continued for 16 hours at room temperature. The reaction mixture was concentrated to dryness under reduced pressure to give a brown solid. The residue was dissolved in a minimum amount of ethyl acetate and filtered through silica gel 60 (230–400 mesh) using ethyl acetate as eluent. The eluent was concentrated to dryness. The product was used without further purification.

$^1$H NMR δ: 1.40(s,9H),6.52(d,J=8.8 Hz,1H)7.97(dd,J= 2.4, 8.8 Hz,1H),8.58(d,J=2.4 Hz,1H)

Synthesis of succinimidyl 6-BOC-hydrazinopyridine-3-carboxylate

[Hydrazinecarboxylic acid, 2-[5-[[(2,5-dioxo-1-pyrrolidinyl)oxy]carbonyl]-2-pyridinyl]-, 1,1-dimethylethyl ester]

To a solution of 6-BOC-hydrazinopyridine-3-carboxylic acid (1.45 g; 5.75 mmol) and N-hydroxysuccinimide (0.66 g; 5.75 mmol) in dimethylformamide (15 ml) was added a solution of dicyclohexylcarbodiimide (1.18 g; 5.75 mmol) in dimethylformamide (5 ml). The reaction mixture became cloudy after 1 hour and stirring was continued for 16 hours at room temperature. The reaction mixture was filtered and the filtrate was concentrated to dryness to give a brown solid residue. The residue was dissolved in a minimum amount of ethyl acetate and filtered through silica gel 60 (230–400 mesh) using ethyl acetate as eluant. The eluant was concentrated to dryness to give a pale yellow solid which was recrystallized from ethyl acetate/hexanes; yield 60%; m.p. 169.5°–172° C.;

Analysis: Calculated for $C_{15}H_{18}N_4O_6$; C - 51.43; H - 5.18, N - 15.99 Found: C - 51.81; H - 5.26; N - 15.60.

$^1$H NMR δ: 1.41(s,9H),2.87(s,4H)6.64(d,J=8.8 Hz,1H) 8.08 (dd,J=2.4,8.8 Hz)8.73(d,J=2.4 Hz,1H)

Synthesis of succinimidyl 6-hydrazinopyridine-3-carboxylate hydrochloride

A solution of hydrogen chloride in dioxane was prepared by bubbling anhydrous hydrogen chloride into dioxane (20 ml) at a moderate rate for 10 min. Succinimidyl 6-BOC-hydrazinopyridine-3-carboxylate (100 mg) was dissolved in dioxane (2 ml) and HCl/dioxane (2 ml) was added and the reaction mixture was stirred at room temperature. After 5 minutes the solution became cloudy and a precipitate formed. Stirring was continued for 4 hours. The cloudy reaction mixture was filtered to give 55 mg of a white solid; yield 67%;

Analysis: Calculated for $C_{10}H_{11}ClN_4O_4$; C - 41.87; H - 3.87; Cl - 12.37; N - 19.53; Found: C - 41.92; H - 3.90; Cl - 12.30; N - 19.47.

¹H NMR δ: 2.88(s,4H),7.01(d,J=8.8 Hz,1H)8.19(dd,J=2.4, 8.8 Hz,1H)8.83(d,J=2.4 Hz,1H)

Example 3

Preparation of succinimidyl 4-hydraziodoterephthalate hydrochloride

[Benzoic acid, 4-[[(2,5-dioxo-1-pyrrolidinyl) oxy] carbonyl]-, hydrazide, monohydrochloride]

Mono-methyl terephthalate, oxalyl chloride, t-butyl carbazate, dicyclohexylcarbodiimide (DCC) and N-hydroxysuccinimide (NHS) were purchased from Aldrich Chemicals (Milwaukee, Wis.).

Synthesis of methyl terephthalate chloride

To a stirred solution of mono-methyl terephthalate (1 equivalent), toluene (30 ml/gm of ester) and 3 drops of DMF was added dropwise oxalyl chloride (2.0 equivalents). The reaction mixture was stirred at 45° C. for 16 hours. The solution was concentrated under reduced pressure to give the desired product as a pale yellow solid. The product was used without further purification; yield 82.0%; m.p. 50°–52° C. IR (thin film); 2970, 1775, 1720, 1430, 1400, 1280, 1105, 880 cm$^{-1}$.

¹H NMR δ: 3.97(s,3H),8.14(s,4H).

Synthesis of methyl 4-BOC-hydrazidoterephthalate [1,4-benzene-dicarboxylic acid, monomethyl ester, 2-[(1,1-dimethylethoxy) carbonyl]hydrazide]

To a vigorously stirred mixture of t-butyl carbazate (1 equivalent), methylene chloride (20 ml/gm) and 25% sodium bicarbonate (2.0 equivalents) was added dropwise a solution of methyl terephthalate chloride (1 equivalent) in methylene chloride (40 ml/gm). The reaction mixture was stirred at 20° for ½ hour. The phases were separated and the aqueous phase was extracted with methylene chloride. The combined organic phases were washed with 10% hydrochloric acid and brine. The organic phase dried (MgSO$_4$), filtered and concentrated to give a white solid; yield 91.7%; m.p. 197°–199°. IR (KBr): 3010, 1720, 1670, 1430, 1270, 1220, 1130, 1100, 1030, 870, 750 cm$^{-1}$.

¹H NMR(CDCl$_3$):δ1.49(s,9H),3.93(s,3H),7.83(d,J$_{AB}$=8 Hz,2H),8.07 (d,J$_{AB}$=8 Hz,2H).

Synthesis of 4-BOC-hydrazidoterephthalic acid

To a solution of methyl 4-BOC-hydrazidoterephthalate (1 equivalent) in methanol (50 ml/gm) was added sodium hydroxide (10.0 equivalents). The reaction was stirred at room temperature for 16 hours. The reaction mixture was concentrated under reduced pressure to remove the methanol. Water was added and the solution was carefully acidified to pH 1.0. The acidic solution was extracted with ethyl acetate and the organic extract was dried (MgSO$_4$), filtered and concentrated to dryness under reduced pressure to give a white solid; yield 87.5%; m.p. 208°–210°.

¹H NMR δ: 1.41 (s,9H),7.97(d,J=2.4 Hz,4H),8.90(m,1H) 10.3(m,1H).

Synthesis of succinimidyl 4-BOC-hydrazidoterephthalate [Hydrazinecarboxylic acid, 2-[4-[[(2,5-dioxo-1-pyrrolidinyl)oxy]carbonyl] benzoyl]-, 1,1-dimethylethyl ester]

To a solution of 4-BOC-hydrazido-terephthalic acid (1 equivalent) and N-hydroxysuccinimide (1 equivalent) in DMF (10 ml/gm) was added dropwise a solution of DCC (1 equivalent) in DMF (5 ml/gm). The reaction mixture was stirred at 20° for 16 hours. Acetic acid (0.5 ml) was then added and stirring was continued for 1 hour. The reaction mixture was filtered to remove the urea byproduct. The filtrate was concentrated under reduced pressure to give a yellow brown oil. Flash vacuum chromatography (hexanes/ ethyl acetate (7/3)) was used to isolate the product; yield 47.8%, m.p. 182°–185°. IR (KBr): 3330, 3230, 2990, 1770, 1740, 1660, 1530, 1500, 1370, 1280, 1200, 1150, 1070, 1000, 870, 790, 640 cm$^{-1}$.

¹H NMR (CDCl$_3$) δ: 1.50(s,9H),2.91(s,4H),6.70(m,1H), 7.91(d,J$_{AB}$=8.8 Hz, 2H), 8.20(d,J$_{AB}$=8.8 Hz,2H).

Analysis: Calculated for C$_{17}$H$_{19}$N$_3$O$_7$: C - 54.11; H - 5.07; N - 11.13; Found: C - 53.66; H - 5.15; N - 11.09.

Synthesis of succinimidyl-4-hydrazidoterephthalate hydrochloride

To a solution of hydrogen chloride in tetrahydrofuran (50 ml/gm; prepared by bubbling hydrogen chloride into tetrahydrofuran for approximately ten minutes) was added succinimidyl 4-BOC-hydrazidoterephthalate (1 equivalent). The reaction mixture was homogeneous for 1 hour; then over 4 hours a pale white precipitate formed. The reaction mixture was filtered and washed with ether to give the desired product as a pale white solid; yield 37.7%; m.p. 278°–280°. IR(KBr): 3400, 3200, 2800, 2600, 1770, 1730, 1690, 1530, 1490, 1290, 1240, 1070, 1000, 870, 730, 640, 610 cm$^{-1}$.

¹H NMR δ: 2.91 (s,4H),8.11(d,J$_{AB}$=8.8 Hz,2H),8.25(d, J$_{AB}$=8.8 Hz,2H).

Analysis: Calculated for C$_{12}$H$_{12}$ClN$_3$O$_5$: C - 45.95; H - 3.86; Cl - 11.30; N - 13.40; Found: C - 45.84; H - 3.91; Cl - 11.37; N - 13.33.

Example 4

Preparation of 5-maleimidyl-2-hydrazinopyridine hydrochloride [1H-pyrrole-2,5-dione, 1-(6-hydrazino-3-pyridinyl)-, monohydrochloride]

2-chloro-5-nitropyridine, hydrazine hydrate, di-tert-butyl dicarbonate, 10% palladium on charcoal, maleic anhydride, cobalt acetate and acetic anhydride were purchased from Aldrich Chemicals (Milwaukee, Wis.).

Synthesis of 2-hydrazino-5-nitropyridine

To a stirred solution of hydrazine hydrate (30.0 equivalents), water (4 ml/gm of pyridine), and ethanol (2 ml/gm of pyridine) was added 2-chloro-5-nitropyridine (1 equivalent). The reaction mixture was stirred at 20° for 16 hours (a very thick green slurry forms). The precipitate was isolated by filtration and the solid was washed with methanol and then ether to give a green solid. The product was used without further purification; yield 77.3%; m.p. 205°–207°. IR (KBr): 3340, 3200, 2980, 1670, 1605, 1580, 1485, 1420, 1330, 1300, 1120, 980, 830, 770 cm$^{-1}$.

¹H NMR δ: 4.64(br s,2H),6.76(d,J=8.8 Hz,1H),8.15(dd, J=2.4,8.8 Hz,1H), 8.86(d,J=2.4 Hz,1H),9.12,(m,1H).

Analysis: Calculated for C$_5$H$_6$N$_4$O$_2$: C - 39.21; H - 3.93; N - 36.51; Found: C - 38.96; H - 3.92; N - 36.35.

Synthesis of 2-(BOC-hydrazino)-5-nitropyridine

To a stirred solution of 2-hydrazino-5-nitropyridine (1 equivalent), DMF (15 ml/gm of pyridine), and triethylamine (1.1 equivalents) was added dropwise a solution of di-tert-butyl dicarbonate (1.0 equivalent) in DMF (4 ml/gm of dicarbonate). The reaction mixture was stirred at 20° for 48 hours. The reaction mixture was concentrated under reduced pressure to a yellow brown oil. Flash vacuum chromatography (hexanes/ethyl acetate (8/2)) was used to isolate the product. The product was recrystallized from ethyl acetate/hexanes; yield 63.4%; m.p. 135°–137°. IR (KBr): 3280, 2980, 1710, 1600, 1500, 1330, 1290, 1270, 1250, 1150, 1120, 1010, 830, 760, 650, 500 cm$^{-1}$.

$^1$H NMR δ: 1.41(s,9H),6.60(d,$J_{AB}$=8.8 Hz,1H),8.28(dd, J=2.4,8.8 Hz,1H), 8.93(d,$J_{AB}$=2.4 Hz,1H),9.14(m,1H),9.56 (m,1H).

Analysis: Calculated for $C_{10}H_{14}N_4O_4$: C - 47.24; H - 5.55; N - 22.03; Found: C - 46.99; H - 5.50; N - 21.93.

Synthesis of 2-(BOC-hydrazino)-5-amino-pyridine

Into a Parr hydrogenation bottle was added 2-BOC-hydrazino-5-nitropyridine (1 equivalent), 10% palladium on charcoal (0.3 gm Pd/gm of pyridine) and ethanol (100 ml/gm of pyridine). The reaction was hydrogenated at 50 psi $H_2$ for 2 hours at room temperature on a Parr hydrogenator. The reaction mixture was filtered through a filter cell plug and rinsed with ethanol. The yellow green solution was concentrated under reduced pressure to give a pale yellow solid. The product was recrystallized from ethanol; yield 81.64%; m.p. 140°–142°. IR (KBr): 3360, 3200, 2980, 1650, 1635, 1580, 1490, 1390, 1360, 1300, 1260, 1160, 1020, 880, 860, 830, 750, 590, 530 cm$^{-1}$.

$^1$H NMR δ: 1.37(s,9H),6.34(d,J=8.8 Hz,1H),6.89(dd,J= 2.4,8.8 Hz,1H), 7.14(m,1H),7.49(d,J=2.4 Hz,1H),8.50(m, 1H).

Analysis: Calculated for $C_{10}H_{16}N_4O_2$: C - 53.55; H - 7.19; N - 24.98; Found: C - 53.73; H - 7.21; N - 25.05.

Synthesis of 2-BOC-hydrazino-5-maleimidylpyridine [Hydrazinecarboxylic acid, 2-[5-(2,5-dihydro-2,5-dioxo-1H-pyrrol-1-yl)-2-pyridinyl]-, 1,1-dimethylethyl ester]

To a stirred solution of 2-BOC-hydrazino-5-amino pyridine (1 equivalent) in acetone (50 ml/gm) was added maleic anhydride (1.1 equivalents). The reaction mixture was stirred at 25° for 2 hours. To the reaction mixture was added acetic anhydride (1.2 equivalents), cobalt acetate (0.007 equivalents) and triethylamine (0.3 equivalents). The reaction mixture was stirred at 60° for 2 hours. The color of the reaction began as bright yellow and ended as dark yellow. The reaction mixture was concentrated under reduced pressure to give a yellow brown oil. Flash vacuum chromatography (hexanes/ethyl acetate (8/2)) was used to isolate the product. The product was recrystallized in ether/hexane; yield 28.3%; m.p. 182°–184°. IR (KBr): 3400, 3300, 3100, 2990, 1700, 1610, 1500, 1410, 1360, 1320, 1270, 1210, 1150, 1050, 830, 750, 690 cm$^{-1}$.

$^1$H NMR δ: 1.39(s,9H),6.58(d,J=8.8 Hz,1H),7.14(s,2H), 7.45 (dd,J=2.4,8.8 Hz,1H),7.94(d,J=2.4 Hz,1H),8.37(m,1H).

Analysis: Calculated for $C_{14}H_{16}N_4O_4$: C - 55.26; H - 5.30; N - 18.41; Found: C - 55.14; H - 5.30; N - 18.33.

Synthesis of 5-maleimidyl-2-hydrazinopyridine hydrochloride

A solution of hydrogen chloride in dioxane was prepared by bubbling anhydrous hydrogen chloride into dioxane (50 ml) at a moderate rate for 10 minutes. 2-(BOC-hydrazino)-5-maleimidylpyridine (200 mg) was dissolved in dioxane (5 ml) and HCl/dioxane (10 ml) was added and the reaction mixture was stirred at room temperature. After 30 minutes the solution became cloudy and a precipitate formed. The reaction mixture was stirred at 25° for a total of 5 hours. The slurry was filtered and washed with ether to give 50 mg of a white solid; yield 31.6%; m.p. 280°–290° (decomp.; yellow to brown). IR (KBr): 3440, 3100, 2580, 1720, 1610, 1560, 1480, 1390, 1200, 1150, 830, 690 cm$^{-1}$.

$^1$H NMR δ: 7.0(d,J=8.8 Hz,1H),7.19(s,2H),7.63(dd,J=2.4, 8.8 Hz,1H), 8.15(d,J=2.4 Hz,1H).

Mass spectrum: m/z=204 (M–HCl)$^+$.

Example 5

Preparation of Succinimidyl 2-(2-propenylhydrazone)nicotinate [Propanal, [5-[[(2,5-dioxo-1-pyrrolidinyl)oxy]carbonyl]-2-pyridinyl] hydrazone].

6-Hydrazinonicotinic acid was prepared as previously described, and propionaldehyde was purchased from Aldrich Chemicals (Milwaukee, Wis.).

Synthesis of Succinimidyl 2-(2-propenylhydrazone) nicotinate

To a suspension of 6-hydrazinonicotinic acid (1 equivalent) in DMF (40 ml/g) was added propionaldehyde (3 equivalents). The reaction mixture was stirred at ambient temperature for 1 hour. If the reaction mixture did not become homogeneous the flask was gently heated with a heat gun until the reaction mixture became homogeneous. The reaction mixture was cooled to ambient temperature and a solution of N-hydroxysuccinimide (1 equivalent) in DMF was added. Subsequently a solution of DCC (1 equivalent) in DMF was added dropwise. The reaction mixture was stirred for 16 hours at ambient temperature. The precipitate which formed was removed by suction filtration and the mother liquors were concentrated to dryness. The brown solid residue was suspended in ethyl acetate and stirred for 1 hour and filtered. A pale brown solid precipitated from the ethyl acetate solution and was isolated by filtration to give the desired product; yield 65%.

$^1$H NMR δ: 1.06(t,3H),2.34(m,2H),2.86(s,4H),7.11(d,J= 9.4 Hz,1H),7.54 (t,1H,J=4.9 Hz),8.10(dd,J=9.44,2.33 Hz,1H),8.72(d,J=2.33 Hz,1H)

Analysis: Calculated for $C_{13}H_{14}N_4O_4$: C - 53.79; H - 4.86; N - 19.30; Found: C - 53.66; H - 4.89; N - 19.12.

Example 6

Preparation of Succinimidyl 2-(2-(1-propenyl) hydrazone))-thiazole-4-carboxylate [Propanal, [4-[[(2,5-dioxo-1-pyrrolidinyl)oxy]carbonyl]-2-thiazolyl] hydrazone]

Thiosemicarbazide and bromolactic acid were purchased from Aldrich Chemicals (Milwaukee, Wis.).

Synthesis of Propionaldehyde Thiosemicarbazone

To a solution of thiosemicarbazide (1 equivalent) and propionaldehyde (1.5 equivalents) in MeOH was added a few drops of glacial acetic acid. The mixture was heated to reflux for 45 minutes. The reaction mixture was concentrated on the rotovap which caused a precipitate to form. The solids were isolated by filtration, washed with ether and dried in vacuo; yield 71%

Synthesis of 2-(2-(1-propenylhydrazone))thiazole-4-carboxylic acid hydrobromide

To a solution of propionaldehyde thiosemicarbazone (1 equivalent) in MeOH was added bromolactic acid (1 equivalent). The reaction mixture was heated at reflux for 1 hour, then cooled to room temperature and the solvent was removed on the rotavap. The resulting yellow solid was triturated with MeOH/ether and a pale yellow solid was isolated and washed with ether and dried in vacuo.

$^1$H NMR δ: 1.00(t,J=7.9 Hz,3H),2.15(m,2H),7.44(t,J=4.9 Hz).

Synthesis of Succinimidyl 2-(2-(1-propenyl) hydrazone)-thiazole-4-carboxylate

To a solution of acid (1 equivalent), N-hydroxysuccinimide (1 equivalent) and triethylamine (1.5 equivalents) in DMF was added dropwise a solution of DCC (1 equivalent) in DMF. The reaction mixture was stirred for 16 hours at room temperature. The precipitate which formed was removed by filtration and the mother liquors were concentrated to dryness. Ethyl acetate was added to the residue and stirred for 1 hour. The insolubles were removed by filtration and the mother liquor was concentrated to dryness. The product was flash chromatographed using hexanes/ethyl acetate (1/2) as eluant to give the desired product as an off-white solid; yield 35%.

$^1$H NMR δ: 1.08(t,J=7.9 Hz,3H),2.24(m,2H),7.40(t,J=4.9 Hz,1H),8.11(s,1H).

Example 7

Preparation of succinimidyl 2-(2-methylethenylhydrazone) thiazole-4-carboxylate.

Synthesis of succinimidyl 2-(2-methylethenylhydrazone) thiazole-4-carboxylate 2-(methylethyenylhydrazone)-4-thiazolecarboxylic acid hydrobromide (1 equivalent) (prepared according to the method of H. Johne, D. Seifert, S. Johne and E. Bulka, Pharmazie 33, 259 (1978)) was dissolved in DMF (20 ml/g). N-Hydroxysuccinimide (1 equivalent) and triethylamine (1.5 equivalents) were added. To the homogeneous mixture a solution of DCC (1 equivalent) was added dropwise over 15 minutes. The reaction mixture was stirred for 16 hours at room temperature. The precipitate which formed was removed by filtration and the mother liquor was concentrated to dryness to give an orange-brown solid. The residue was suspended in ethyl acetate and stirred at room temperature for 1 hour. Insolubles were removed by filtration and the mother liquor was concentrated to give a brown solid. The solids were triturated with ether and re-isolated by filtration to give a yellow-brown solid: yield 40%. A sample of the product was filtered through a short plug of silica gel using hexanes/ethyl acetate (2/1) as eluate. The eluant was concentrated to give the desired product as a pale yellow solid; m.p. 202°–205° (decomp.).

$^1$H NMR δ: 1.92(s,3H),1.96(s,3H),2.86(s,4H),8.11(s,1H). Mass spectrum: m/z=297 (M+1)$^+$ Example 8

Preparation of Succinimidyl 4-thiosemicarbazidobenzoate hemihydrochloride [Hydrazinecarbothioamide, N-[4-[[(2,5-dioxo-1-pyrrolidinyl)oxy]carbonyl]phenyl]-, hemihydrochloride].

4-Aminocarboxylic acid was purchased from Aldrich Chemicals (Milwaukee, Wis.).

Synthesis of BOC-4-thiosemicarbazidobenzoic acid [Hydrazinecarboxylic acid, 2-[[(4-carboxyphenyl) amino]thioxomethyl]-, 1-(1,1-dimethylethyl) ester]

To a solution of 4-isothiocyanatobenzoic acid (1 equivalent) (prepared according to the method of D. W. Browne and G. M. Dyson, J.Chem.Soc. 178 (1934)) and triethylamine (1.2 equivalents) in DMF was added to a solution of t-butyl carbazate (1 equivalent). The reaction mixture was stirred at room temperature for 3 hours and subsequently concentrated to dryness. The residue was dissolved in ethyl acetate and washed with 10% citric acid and brine. The organic phase was dried (MgSO$_4$), filtered and concentrated to give the desired product as an off-white solid; yield 70%; m.p. 131°–133° (decomp.).

$^1$H NMR δ: 1.42(s,9H),7.67(d,J$_{AB}$=8.9 Hz,2H),7.87(d, J$_{AB}$=8.9 Hz,2H).

Synthesis of Succinimidyl BOC-4-thiosemicarbazidobenzoate [Hydrazinecarboxylic acid, 2-[[[4-[[(2,5-dioxo-1-pyrrolidinyl)oxy] carbonyl]phenyl]amino]thioxomethyl]-1,1-dimethylethyl ester]

To a solution of acid (1 equivalent) and N-methylmorpholine (1.1 equivalents) in acetonitrile was added a solution of succinimidyl tetrachloroethyl carbonate (1 equivalent) in acetonitrile. The reaction mixture was stirred at room temperature for 16 hours. Ethyl acetate was added to the reaction mixture and the homogeneous solution was washed with cold 5% citric acid, cold water, cold aqueous saturated sodium bicarbonate solution, cold water and cold brine. The organic phase was dried (MgSO$_4$), filtered and concentrated to give a pale yellow oil. The oil was flash chromatographed on silica gel using hexanes/ethyl acetate as eluant. The product was isolated as a yellow oil which solidified on the addition of ether. The solids were isolated by filtration to give the desired product; yield 25%; m.p. 161°–163°.

$^1$H NMR δ: 1.52(s,9H),2.88(s,4H),7.74(d,J$_{AB}$=10.0 Hz,2H), 8.05(d,J$_{AB}$=10.0 Hz,2H).

Analysis: Calculated for C$_{17}$H$_{20}$N$_4$SO$_6$: C - 49.99; H - 4.94; N - 13.72 S - 7.85; Found: C - 50.05; H - 4.95; N - 13.64 s - 7.95.

Synthesis of Succinimidyl 4-thiosemicarbazidobenzoate hemihydrochloride

To a suspension of BOC succinimidyl ester in ether was added a solution of dry HCl(g) in ether (prepared by bubbling HCl gas into dry ether). The suspension was stirred at room temperature for 16 hours. The reaction mixture was heterogeneous over the entire course of the reaction. The solids were isolated by filtration to give the desired hydrochloride salt product; yield 80%; m.p. 155°–160°.

$^1$H NMR δ: 2.88(s,4H), 8.01(s,4H).

Analysis: Calculated for C$_{12}$H$_{13}$N$_4$SO$_4$ .0.5 HCl: C - 44.00; H - 4.15; N - 17.10 S - 9.79; Found: C - 44.56; H - 3.88; N - 17.04 S - 9.74.

Example 9

Conjugation of IgG

To a solution of 10 mg IgG (MW=155,000) in 2 ml 0.1M sodium phosphate buffer (pH 7.8) was added 17.2 µl of 30 mM succinimidyl 4-hydrazinobenzoate hydrochloride in dimethylformamide. After stirring for 5 hours at room temperature, the reaction mixture was dialyzed against 0.1M sodium acetate buffer (pH 5.2). The number of hydrazino groups conjugated onto the protein was measured by the method of T. P. King et al. (Biochemistry, 25:5774, 1986). Briefly, the hydrazino-protein conjugate was reacted with 4-nitrobenzaldehyde to convert the hydrazino groups into hydrazones. The number of hydrazones/protein molecule were determined spectrophotometrically using the hydrazone of p-nitrophenylbenzaldehyde and phenylhydrazine ($\lambda_{max}$=412, $\epsilon$=2.41×10$^4$) as a standard. Modification yields of 25–35% were obtained.

Example 10
Labelling of Conjugated IgG with $^{99m}$Tc

A DuPont Tc-glucoscan kit was reconstituted with 3 ml of water containing 10 mCi of $^{99m}$TcO$_4^-$. 250 μl of this solution was mixed with 250 μl of 1–5 mg/ml conjugated IgG in 0.1M sodium acetate buffer (pH 5.2). After incubation for 1 hour at room temperature >95% of the activity was associated with the protein as determined by radiometric HPLC (TSK 3000 column) and instant thin layer chromatography (ITLC.)

800 uCi of Tc labelled IgG was injected into rats containing an abscess in one hind leg. At 24 hours the rats were sacrificed. The distribution of radioactivity was measured:

| Organ | % Injected dose/gram tissue |
| --- | --- |
| Blood | 1.36 |
| Kidney | 1.11 |
| Infected Muscle | 0.76 |
| Normal Muscle | 0.12 |
| Liver | 0.81 |

Ratio Infected/Normal muscle=6.3

Example 11
Conjugation of fragment E$_1$ (DD)E protein was concentrated to between 5–10 mg/ml and modified with a 20-fold molar excess of succinimidyl 6-hydrazinopyridine-3-carboxylate hydrochloride in 12.5 mM borate buffer at pH 8.5. After a 5 hour incubation (with gentle stirring) at 4° C., the sample was dialyzed approximately 12 hours versus degassed nanopure water.

Fragment E$_1$ was separated from the modified DD(E) complex by making the sample 0.55M in acetic acid and diluting 1:1 V/V with 6M urea. The pH of the sample was adjusted to 5.5 with 10N NaOH and the sample was then dialyzed against 10 mM citrate buffer (pH 5.7) to remove excess reagents. During dialysis, DD protein precipitates leaving modified fragment E$_1$ in solution. The DD precipitate was readily removed by centrifugation.

Modified E$_1$ was labelled with Tc-99m via reaction with Tc-99m glucoheptonate, as previously described. The Tc-99m labelled E$_1$ was used to image a thrombus in a rabbit model (see D. Collen et al., J. Clin. Invest. 71, p. 368–376 (1983)).

Example 12
Conjugation of monoclonal antibody 5E8 (see E. A. Chen et al, Cancer Research, 49, p. 3642–3649 (1989)).

5E8 (at a concentration of 5–10 mg/ml) was modified with a 14-fold excess of succinimidyl 6-hydrazinopyridine-3-carboxylate hydrochloride in 12.5 mM borate buffer at pH 8.5 (5 hours at room temperature). The antibody conjugate was dialyzed against a 20 mM citrate buffer (pH 5.2 100 mM in NaCl). After centrifugation to remove a small amount of turbidity, the degree of modification (determined spectrophotometrically, as previously described) was found to be 6.5 hydrazine groups per protein molecule. Analysis by ELISA and immunocytoadherence showed no loss in immunoreactivity.

The specific compounds and details of the method described above are exemplary and are not intended to limit the scope of the invention.

We claim:

1. A conjugate formed by reaction of a biologically useful macromolecule selected from the group consisting of a protein, glycoprotein and peptide, with a hydrazine compound of the formula (I) or (II):

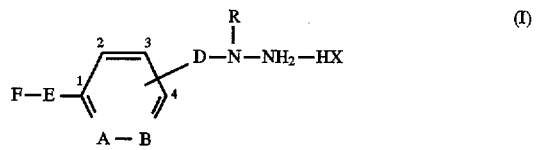

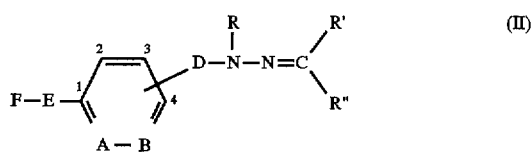

wherein:

A is a carbon or nitrogen atom;

B is a carbon or nitrogen atom;

D is a direct bond, CH$_2$, C=O or

E is C=O or together with F forms a maleimidyl group;

F is a group readily replaced by a primary amine in neutral or basic aqueous media when E is C=O or together with E forms a maleimidyl group;

R is hydrogen or a lower alkyl group;

R' and R" may be the same or different and are selected from hydrogen and lower alkyl; and X is a negative counterion, the conjugate being formed by reaction of nucleophilic groups of the macromolecule with the hydrazine or hydrazide compound through the F-E-substituent.

2. The conjugate of claim 1 wherein D is a direct bond to the 4-position of the ring.

3. The conjugate of claim 2 wherein E is carbonyl and F is selected from the group consisting of N-oxysuccinimidyl, tetrafluorophenolate, N-oxybenztriazole and imidazolate, and X is selected from the group consisting of halides, nitrate, trifluoroacetate, tetrafluoroborate and sulfate.

4. The conjugate of claim 2 wherein R is hydrogen or methyl, E is carbonyl, F is N-oxysuccinimidyl, and X is Cl.

5. The conjugate of claim 4 wherein both A and B are carbon atoms or one of A and B is carbon and the other is nitrogen.

6. The conjugate of claim 4 wherein A is carbon, B is nitrogen, and R is hydrogen.

7. The conjugate of claim 4 wherein A and B are nitrogen atoms and R is hydrogen.

8. The conjugate of claim 1 wherein D is C=O, CH$_2$ or thioamide

and is attached to the 4-position of the ring.

9. The conjugate of claim 8 wherein D is C=O or thioamide.

10. The conjugate of claim 9 wherein E is C=O and F is selected from the group consisting of N-oxysuccinimidyl, tetrafluorophenolate, N-oxybenztriazole and imidazolate and X is selected from the group consisting of halides, nitrate, trifluoroacetate, tetrafluoroborate and sulfate.

11. The conjugate of claim 8 wherein D and E are carbonyl, F is N-oxysuccinimidyl and X is Cl.

12. The conjugate of claim 8 wherein D is thioamide, E is carbonyl, F is N-oxysuccinimidyl and X is Cl.

13. The conjugate of claim 2 wherein E is carbonyl, F is N-oxysuccinimidyl, A is carbon, B is nitrogen, R and R' are hydrogen, and R" is ethyl.

14. A hydrazine conjugate of the type:

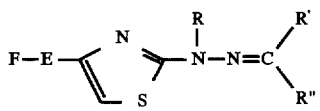

where F, E, R, R' and R" are defined as in claim 1.

15. A conjugate of claim 14 wherein E is carbonyl, F is N-oxysuccinimidyl, R' is hydrogen and R" is ethyl.

16. A conjugate of claim 15 wherein E is carbonyl, F is N-oxysuccinimidyl, and both R' and R" are methyl.

17. The conjugate of claim 1, wherein said macromolecule comprises an immunoglobulin or a fragment thereof.

18. A conjugate according to claim 1 wherein the macromolecule is a monoclonal antibody.

* * * * *